(12) United States Patent
Lee et al.

(10) Patent No.: US 12,631,608 B2
(45) Date of Patent: May 19, 2026

(54) DEVICE FOR COLLECTING ODOR DATA AND METHOD FOR COLLECTING ODOR DATA USING THE SAME

(71) Applicants: Hyundai Motor Company, Seoul (KR); Kia Corporation, Seoul (KR)

(72) Inventors: Tae Hee Lee, Yongin-si (KR); Dae Un Sung, Incheon (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 401 days.

(21) Appl. No.: 18/479,388

(22) Filed: Oct. 2, 2023

(65) Prior Publication Data

US 2024/0369521 A1 Nov. 7, 2024

(30) Foreign Application Priority Data

May 3, 2023 (KR) ........................ 10-2023-0057423

(51) Int. Cl.
*G01N 33/00* (2006.01)

(52) U.S. Cl.
CPC ....... *G01N 33/0006* (2013.01); *G01N 33/007* (2013.01)

(58) Field of Classification Search
CPC ......................... G01N 33/007; G01N 33/0006
See application file for complete search history.

(56) References Cited

U.S. PATENT DOCUMENTS

| | | | |
|---|---|---|---|
| 5,627,307 A | 5/1997 | Hayashi | |
| 6,277,649 B1 | 8/2001 | Markelov | |
| 2013/0061692 A1 | 3/2013 | Muresan | |
| 2014/0099729 A1 | 4/2014 | Mershin | |
| 2017/0368904 A1 | 12/2017 | Seong | |
| 2018/0110457 A1 | 4/2018 | Smith | |
| 2021/0096115 A1* | 4/2021 | König | G01N 33/0016 |
| 2021/0131903 A1* | 5/2021 | Ghasemvand | G01F 25/10 |
| 2022/0178895 A1* | 6/2022 | Tschuncky | G01N 33/0006 |

FOREIGN PATENT DOCUMENTS

| | | | | |
|---|---|---|---|---|
| CN | 111812279 A | * | 10/2020 | G01N 33/007 |
| CN | 112710788 A | * | 4/2021 | G01N 33/0006 |

OTHER PUBLICATIONS

Machine translation of CN 111812279 (Year: 2020).*
Machine translation of CN 112710788 (Year: 2021).*

* cited by examiner

*Primary Examiner* — Nathaniel J Kolb
(74) *Attorney, Agent, or Firm* — Slater Matsil, LLP

(57) ABSTRACT

An embodiment device for collecting odor data includes an odor measurement chamber including a gas injection hole, a first gas circulation line and a second gas circulation line selectively connected to the odor measurement chamber, internal odor sensors disposed in the odor measurement chamber, wherein the internal odor sensors are of different types from each other, and an external odor sensor disposed outside the odor measurement chamber and connected to the first gas circulation line and the second gas circulation line.

19 Claims, 5 Drawing Sheets

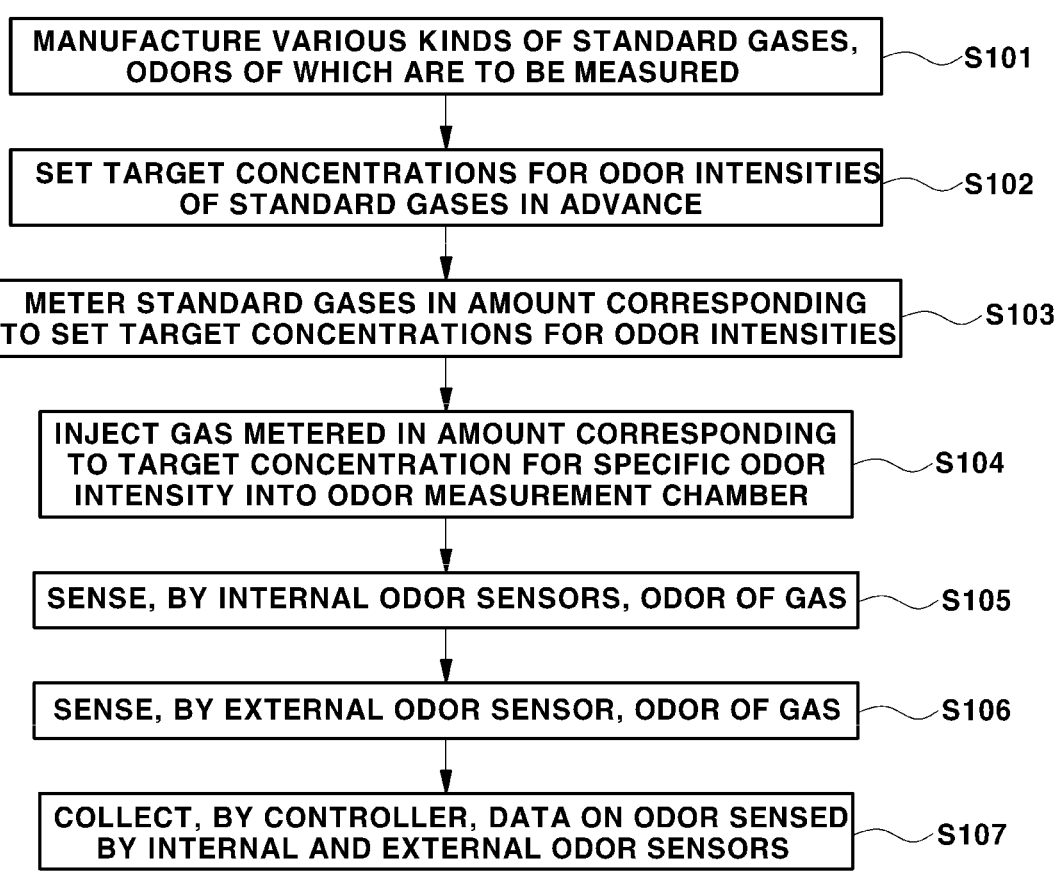

MANUFACTURE VARIOUS KINDS OF STANDARD GASES, ODORS OF WHICH ARE TO BE MEASURED — S101

SET TARGET CONCENTRATIONS FOR ODOR INTENSITIES OF STANDARD GASES IN ADVANCE — S102

METER STANDARD GASES IN AMOUNT CORRESPONDING TO SET TARGET CONCENTRATIONS FOR ODOR INTENSITIES — S103

INJECT GAS METERED IN AMOUNT CORRESPONDING TO TARGET CONCENTRATION FOR SPECIFIC ODOR INTENSITY INTO ODOR MEASUREMENT CHAMBER — S104

SENSE, BY INTERNAL ODOR SENSORS, ODOR OF GAS — S105

SENSE, BY EXTERNAL ODOR SENSOR, ODOR OF GAS — S106

COLLECT, BY CONTROLLER, DATA ON ODOR SENSED BY INTERNAL AND EXTERNAL ODOR SENSORS — S107

DEVICE FOR COLLECTING ODOR DATA AND METHOD FOR COLLECTING ODOR DATA USING THE SAME

CROSS-REFERENCE TO RELATED APPLICATIONS

This application claims the benefit of Korean Patent Application No. 10-2023-0057423, filed on May 3, 2023, which application is hereby incorporated herein by reference.

TECHNICAL FIELD

The present disclosure relates to a device and method for collecting odor data.

BACKGROUND

As is well known, inherent odors and volatile organic compound (VOC) odors generated from various interior parts of vehicles, such as seat covers, head linings, door trims, and mats, are major causes of complaints about new vehicles.

In addition, an odor due to mold propagation caused by moisture condensed in an evaporator core during operation of an air conditioner of a vehicle also causes discomfort to vehicle users.

In addition, various kinds of odors may be included in external air flowing into vehicles during travel depending on the surrounding environment, and the odors introduced into vehicles from outside may also give vehicle users an unpleasant feeling.

The emotional quality of vehicles may be degraded due to various kinds of odors generated in the vehicles or introduced thereinto from outside.

Therefore, accurate odor sensing of an odor sensor and construction of odor data are required in order to analyze causes of various kinds of odors generated in vehicles or introduced thereinto from outside and to remove the odors. In addition, it is necessary to analyze the components of various kinds of odors generated in vehicles or introduced thereinto from outside and concentrations of the odor components in order to clearly identify actual causes of the odors.

In addition, in order to settle civil complaints related to odors generated in various industrial sites as well as in vehicles, it is necessary to accurately measure the components of odors and concentrations of the odor components by installing odor sensors in the corresponding industrial sites.

To this end, as conventional odor sensors for measuring odors generated in various industrial sites as well as in vehicles, electrochemical odor sensors or electrochemical odor sensor arrays may be used. Alternatively, odor biosensors, such as biopeptide-type sensors or sensors using amino acid, may be used. Odor sensors having various other structures are being developed.

However, various types of odor sensors have mutually different levels of sensing response performance and accuracy. Therefore, there is a limitation in accurately collecting odor data. In addition, it is impossible to accurately determine the intensity and kind of odor based on collected odor data.

The above information disclosed in this background section is only for enhancement of understanding of the background of embodiments of the invention, and therefore it may contain information that does not form the related art that is already known to a person of ordinary skill in the art.

SUMMARY

The present disclosure relates to a device and method for collecting odor data. Particular embodiments relate to an odor data collection device and method capable of constructing standard data for determination of the intensity and kind of odor using odors measured from various kinds of gases.

Embodiments of the present invention can solve problems associated with the related art, and embodiments of the present invention provide a device and method for collecting odor data, in which target concentrations for odor intensities of various kinds of gases, odors of which are to be measured, are set in advance, a specific gas is metered in an amount corresponding to a target concentration and then is injected into an odor measurement chamber in which different types of odor sensors are disposed, and the odor sensors sense an odor of the gas in order to collect data on the sensed odor, whereby the collected odor data may be used as standard data for determination of the intensity and kind of odor or may be used as data for training artificial intelligence robots or the like.

An embodiment of the present invention provides a device for collecting odor data, the device including an odor measurement chamber including a gas injection hole formed therein, a first gas circulation line and a second gas circulation line selectively connected to the odor measurement chamber so as to communicate with the odor measurement chamber, two or more different types of internal odor sensors disposed in the odor measurement chamber, and an external odor sensor disposed outside the odor measurement chamber and connected to the first gas circulation line and the second gas circulation line.

In a preferred embodiment, the device for collecting odor data may further include an injector connected to the gas injection hole in order to inject a gas, an odor of which is to be measured, into the odor measurement chamber.

In another preferred embodiment, the injector may be filled with a gas metered in an amount corresponding to a target concentration for preset odor intensity.

In still another preferred embodiment, each of the two or more different types of internal odor sensors may include a first case including a gas inlet and a gas outlet formed in respective ends thereof, a first odor sensing portion disposed in the first case so as to be located between the gas inlet and the gas outlet to sense an odor of a gas, and a gas flow induction fan mounted in the gas inlet or the gas outlet.

In yet another preferred embodiment, the external odor sensor may include a second case including a gas inlet and a gas outlet formed in respective ends thereof, first connectors mounted to the gas inlet and the gas outlet so as to be coupled to second connectors mounted to the first gas circulation line and the second gas circulation line, respectively, a second odor sensing portion disposed in the second case so as to be located between the gas inlet and the gas outlet to sense an odor of a gas, and a pump mounted in the gas inlet or the gas outlet to circulate a gas in the odor measurement chamber so that the gas sequentially flows through the first gas circulation line, the second odor sensing portion, and the second gas circulation line and returns back to the odor measurement chamber.

In still yet another preferred embodiment, the device for collecting odor data may further include a controller configured to collect data on an odor sensed by the two or more different types of internal odor sensors and the external odor sensor.

In a further preferred embodiment, the device for collecting odor data may further include an opening/closing door mounted on one side portion of the odor measurement chamber in order to secure a passage for replacement of the two or more different types of internal odor sensors.

Another embodiment of the present invention provides a method of collecting odor data, the method including injecting a gas metered in an amount corresponding to a target concentration for preset odor intensity into an odor measurement chamber, sensing, by two or more different types of internal odor sensors disposed in the odor measurement chamber, an odor of the gas, sensing, by an external odor sensor, an odor of the gas when the gas injected into the odor measurement chamber sequentially flows through a first gas circulation line connected to the outside of the odor measurement chamber, the external odor sensor, and a second gas circulation line and returns back to the odor measurement chamber, and collecting, by a controller, data on the odor sensed by the two or more different types of internal odor sensors and the external odor sensor.

In a preferred embodiment, the gas metered in an amount corresponding to a target concentration for preset odor intensity may be obtained through a method including manufacturing various kinds of standard gases, odors of which are to be measured, setting target concentrations for odor intensities of the standard gases in advance, and metering the standard gases in an amount corresponding to the set target concentrations for odor intensities.

In another preferred embodiment, in the injecting a gas metered in an amount corresponding to a target concentration for preset odor intensity into an odor measurement chamber, when a gas metered in an amount corresponding to a target concentration for odor intensity higher by one level is injected into the odor measurement chamber, the gas may be additionally injected into the odor measurement chamber by an amount obtained by subtracting an amount of gas metered so as to correspond to a target concentration for odor intensity lower by one level and previously injected into the odor measurement chamber from an amount of gas metered so as to correspond to a target concentration for odor intensity higher by one level.

Other aspects of preferred embodiments of the invention are discussed infra.

The above and other features of embodiments of the invention are discussed infra.

BRIEF DESCRIPTION OF THE DRAWINGS

The above and other features of embodiments of the present invention will now be described in detail with reference to certain exemplary embodiments thereof illustrated in the accompanying drawings which are given hereinbelow by way of illustration only, and thus are not limitative of the embodiments of the present invention, and wherein:

FIG. 2 is a schematic diagram showing a state in which a gas, an odor of which is to be measured, flows to an internal odor sensor and an external odor sensor in the device for collecting odor data according to embodiments of the present invention;

FIG. 3 is a cross-sectional view showing the internal odor sensor of the device for collecting odor data according to embodiments of the present invention;

FIG. 4 is a cross-sectional view showing the external odor sensor of the device for collecting odor data according to embodiments of the present invention; and FIG. 5 is a flowchart showing a method of collecting odor data according to embodiments of the present invention.

Figure 1:
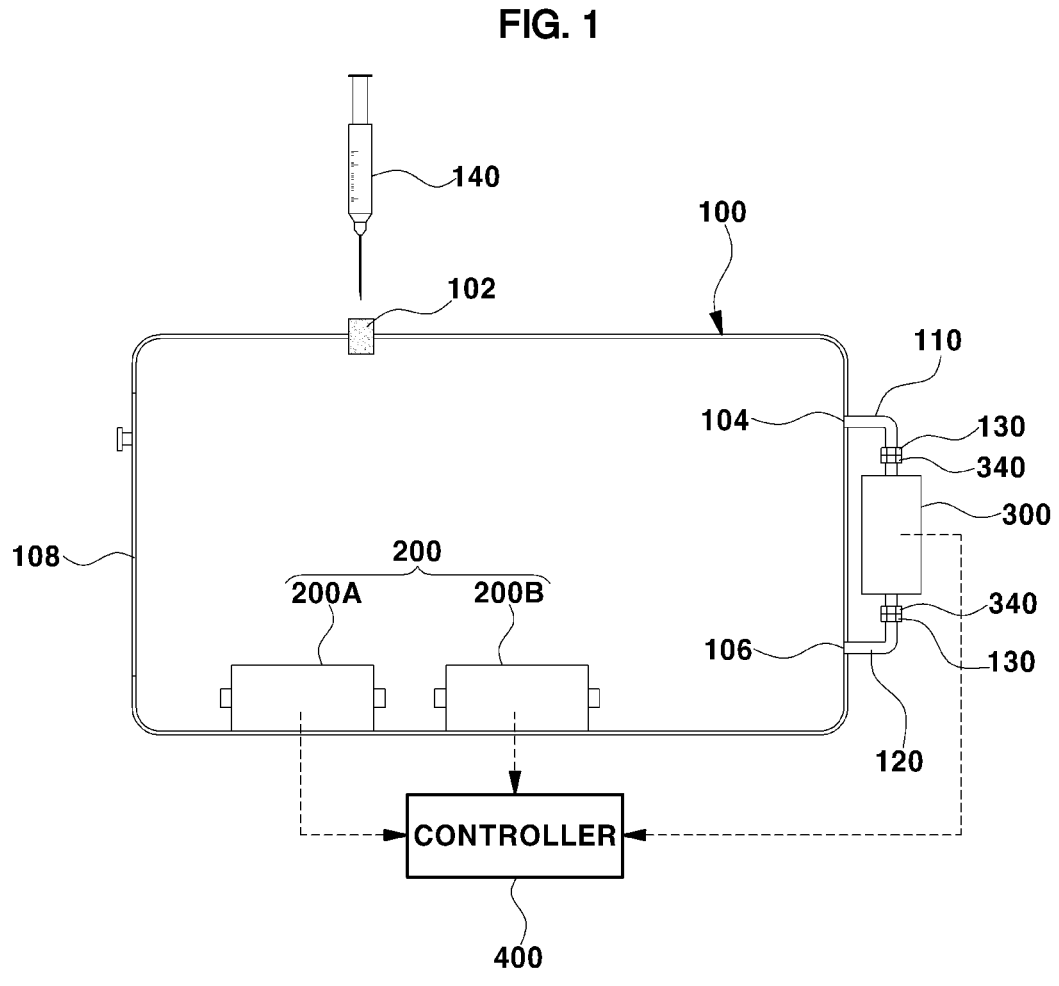
FIG. 1 is a schematic diagram showing a device for collecting odor data according to embodiments of the present invention.

It should be understood that the appended drawings are not necessarily to scale, presenting a somewhat simplified representation of various preferred features illustrative of the basic principles of embodiments of the invention. The specific design features of embodiments of the present invention as disclosed herein, including, for example, specific dimensions, orientations, locations, and shapes, will be determined in part by the particular intended application and use environment.

In the figures, reference numbers refer to the same or equivalent parts of embodiments of the present invention throughout the several figures of the drawings.

DETAILED DESCRIPTION OF ILLUSTRATIVE EMBODIMENTS

Various exemplary embodiments will now be described more fully with reference to the accompanying drawings, in which only some exemplary embodiments are shown. Specific structural and functional details disclosed herein are merely representative for the purpose of describing exemplary embodiments. Embodiments of the present invention, however, may be embodied in many alternate forms, and should not be construed as being limited only to the exemplary embodiments set forth herein. Accordingly, while exemplary embodiments of the invention are capable of being variously modified and taking alternative forms, embodiments thereof are shown by way of example in the drawings and will herein be described in detail. It should be understood, however, that there is no intent to limit the embodiments of the present invention to the particular exemplary embodiments disclosed. On the contrary, exemplary embodiments are to cover all modifications, equivalents, and alternatives falling within the scope of the invention.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the exemplary embodiments of the present invention.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

Wherever possible, the same reference numbers will be used throughout the drawings to refer to the same or like parts. The terminology used herein is for the purpose of describing particular embodiments only and is not intended to be limiting of exemplary embodiments of the invention. As used herein, the singular forms "a", "an", and "the" are intended to include the plural forms as well, unless the context clearly indicates otherwise. It will be further understood that the terms "comprises", "comprising", "includes", and/or "including", when used herein, specify the presence of stated components, steps, operations, and/or elements, but do not preclude the presence or addition of one or more other components, steps, operations, and/or elements.

Hereinafter, exemplary embodiments of the present invention will be described in detail with reference to the accompanying drawings.

Figure 2:
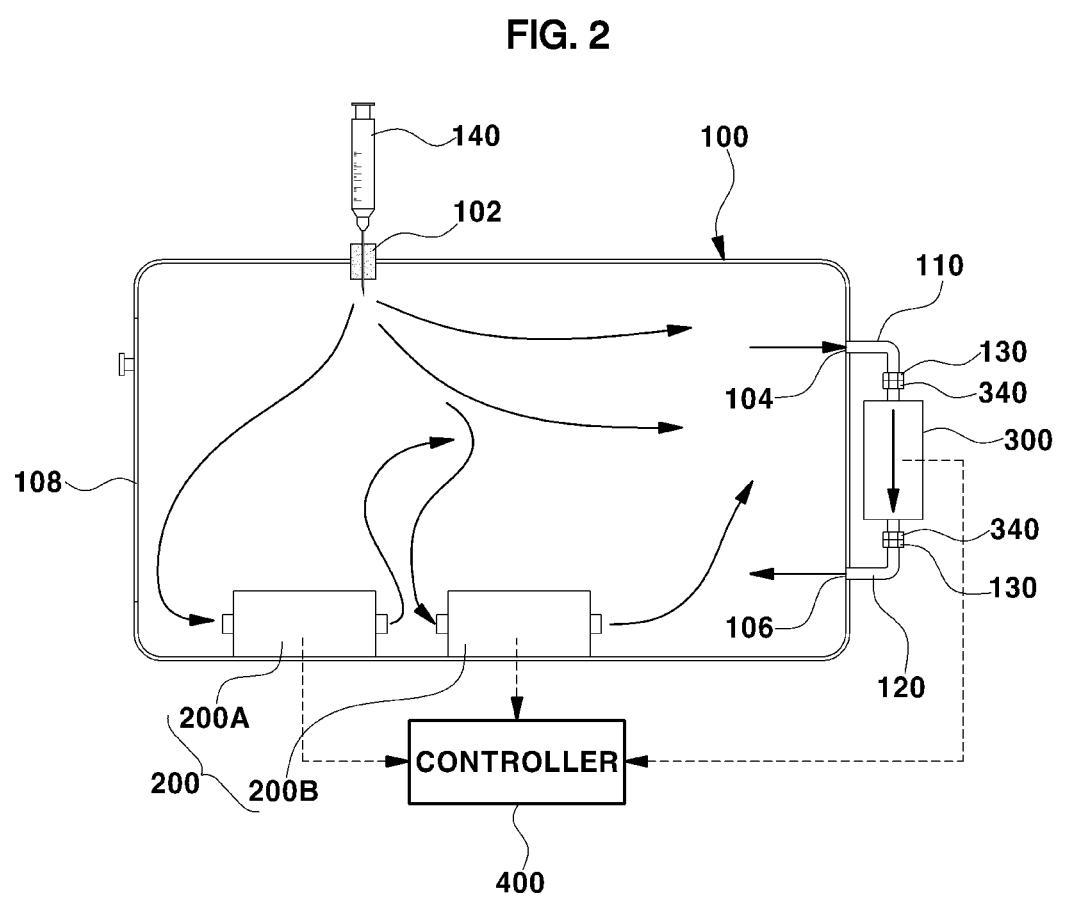

FIGS. 1 and 2 are schematic diagrams showing a device for collecting odor data according to embodiments of the present invention. Reference numeral 100 denotes an odor measurement chamber.

The odor measurement chamber 100 may be manufactured in a sealed box structure having a predetermined internal volume using a transparent plate, such as an acrylic plate.

The odor measurement chamber 100 includes a gas injection hole 102 formed in a predetermined portion of the upper side thereof to inject a gas, an odor of which is to be measured, into the odor measurement chamber 100.

Preferably, a packing member made of rubber or silicone may be inserted into the gas injection hole 102 in order to maintain sealing.

An injector 140 configured to inject the gas, the odor of which is to be measured, into the odor measurement chamber 100 may be connected to the gas injection hole 102 in the odor measurement chamber 100.

For example, the injector 140 is a device such as a syringe and may be filled with a gas metered in an amount corresponding to a target concentration for preset odor intensity.

An injection needle of the injector 140 may be inserted through the packing member in the gas injection hole 102 in order to inject the gas, the odor of which is to be measured, i.e., the gas metered in an amount corresponding to a target concentration for preset odor intensity, which is charged in the injector 140, into the odor measurement chamber 100.

Two or more different types of internal odor sensors 200 may be disposed in the odor measurement chamber 100.

For example, a first internal odor sensor 200A and a second internal odor sensor 200B, which are of different types, may be disposed in the odor measurement chamber 100.

Each of the internal odor sensors 200 has a structure capable of suctioning and discharging a gas and capable of sensing an odor of the suctioned gas.

Figure 3:
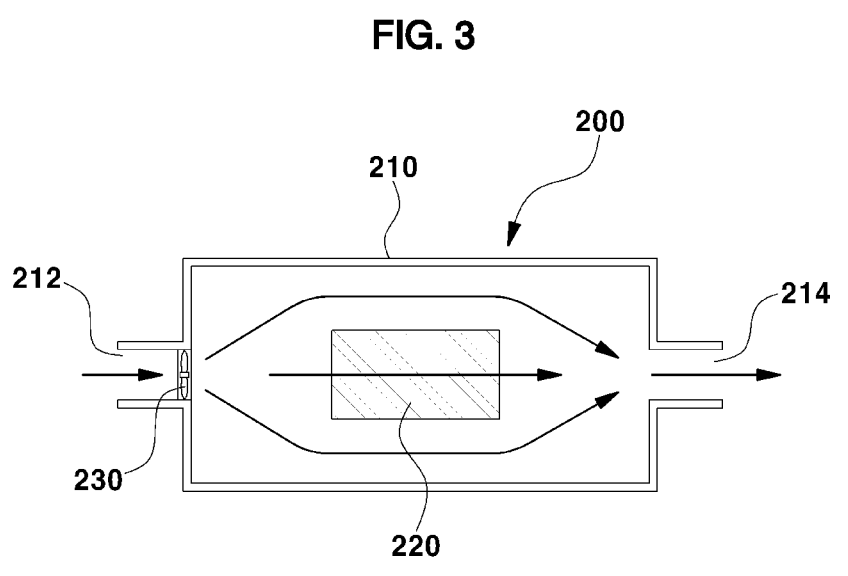

To this end, as shown in FIG. 3, each of the internal odor sensors 200 may include a first case 210, which includes a gas inlet 212 and a gas outlet 214 formed in respective ends thereof, a first odor sensing portion 220, which is mounted in the first case 210 so as to be located between the gas inlet 212 and the gas outlet 214 to sense an odor of a gas, and a gas flow induction fan 230, which is mounted in the gas inlet 212 or the gas outlet 214.

The first case 210 serves to protect the first odor sensing portion 220, which is an odor sensing element, and the gas flow induction fan 230 serves to guide the gas, the odor of which is to be measured, to flow to the gas inlet 212, the first odor sensing portion 220, and the gas outlet 214.

In the case in which the first internal odor sensor 200A and the second internal odor sensor 200B, which are of different types, are disposed in the odor measurement chamber 100, first odor sensing portions 220 having mutually different sensing principles may be mounted in the first internal odor sensor 200A and the second internal odor sensor 200B, respectively. Accordingly, the first internal odor sensor 200A and the second internal odor sensor 200B may be implemented as mutually different types of odor sensors.

When the gas flow induction fan 230 of each of the internal odor sensors 200 is driven, the gas, the odor of which is to be measured, which is injected into the odor measurement chamber 100 through the gas injection hole 102, may enter the gas inlet 212 of the first case 210 and then may flow to the gas outlet 214 via the first odor sensing portion 220. At this time, the first odor sensing portion 220 may sense an odor of the gas.

Preferably, an opening/closing door 108 may be mounted on one side portion of the odor measurement chamber 100 in order to secure a passage for replacement of the internal odor sensors 200. The internal odor sensors 200 may be replaced or an additional odor sensor may be placed in the odor measurement chamber 100 in the state in which the opening/closing door 108 is opened.

Further, an external odor sensor 300 may be selectively connected to the odor measurement chamber 100 so as to sense an odor of the gas.

To this end, a discharge hole 104, through which the gas in the odor measurement chamber 100 is discharged to the outside, and a return hole 106, through which the gas discharged to the outside returns back to the odor measurement chamber 100, are formed in one side portion of the odor measurement chamber 100.

In addition, a first gas circulation line 110 and a second gas circulation line 120 are connected to the discharge hole 104 and the return hole 106 in the odor measurement chamber 100, respectively.

The external odor sensor 300, which is of a different type than the internal odor sensors 200, may be disposed outside the odor measurement chamber 100 so as to be connected between the first gas circulation line 110 and the second gas circulation line 120.

The external odor sensor 300 has a structure capable of circulating a gas along a predetermined path in a manner of suctioning a gas from a gas suction source and discharging the suctioned gas back to the gas suction source.

Figure 4:
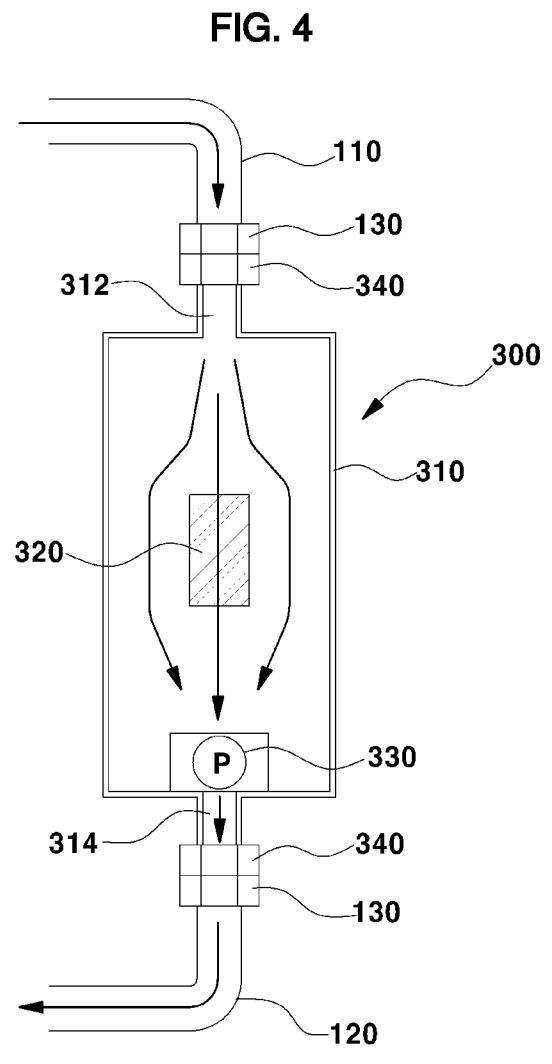

To this end, as shown in FIG. 4, the external odor sensor 300 may include a second case 310, which includes a gas inlet 312 and a gas outlet 314 formed in respective ends thereof, a second odor sensing portion 320, which is mounted in the second case 310 so as to be located between the gas inlet 312 and the gas outlet 314 to sense an odor of a gas, and a pump 330, which is mounted in the gas inlet 312 or the gas outlet 314 to circulate the gas in the odor measurement chamber 100 so that the gas sequentially flows through the first gas circulation line 110, the second odor sensing portion 320, and the second gas circulation line 120 and then returns back to the odor measurement chamber 100.

The second case 310 serves to protect the second odor sensing portion 320, which is an odor sensing element, and the pump 330 serves to circulate the gas, the odor of which is to be measured, along a predetermined path in a manner of suctioning the gas from a gas suction source and discharging the suctioned gas back to the gas suction source.

In addition, the external odor sensor 300 may further include first connectors 340 mounted to the gas inlet 312 and the gas outlet 314 of the second case 310.

The first connectors 340 mounted to the gas inlet 312 and the gas outlet 314 of the second case 310 may be coupled to second connectors 130 mounted to the first gas circulation line 110 and the second gas circulation line 120, respectively, whereby the external odor sensor 300 may be connected between the first gas circulation line 110 and the second gas circulation line 120.

In this case, the first odor sensing portions 220 having mutually different sensing principles may be mounted in the first internal odor sensor 200A and the second internal odor sensor 200B of the internal odor sensors 200, respectively, and the second odor sensing portion 320 having another sensing principle may be mounted in the external odor sensor 300. Accordingly, the first internal odor sensor 200A, the second internal odor sensor 200B, and the external odor sensor 300 may be implemented as mutually different types of odor sensors.

When the pump 330 of the external odor sensor 300 is driven, the gas, the odor of which is to be measured, which is injected into the odor measurement chamber 100, may sequentially flow through the discharge hole 104, the first gas circulation line 110, and the gas inlet 312 of the second case 310 and then may reach the second odor sensing portion 320. At this time, the second odor sensing portion 320 may sense an odor of the gas. Subsequently, the gas that has passed through the second odor sensing portion 320 may sequentially flow through the gas outlet 314, the second gas circulation line 120, and the return hole 106 and then may return back to the odor measurement chamber 100.

Meanwhile, data on the odor sensed by the internal odor sensors 200 and the external odor sensor 300 may be transmitted to and collected in a controller 400.

In this way, the internal odor sensors 200 and the external odor sensor 300, which are of different types, may sense an odor of the same gas at the same time, whereby the sensing performance of the different types of odor sensors may be evaluated at once, and pieces of data on the odor sensed by the respective odor sensors may be collected at once. The collected odor data may be used as odor data for training artificial intelligence robots or the like, or may be used as standard data for determination of the intensity and kind of odor measured by odor measurement devices mounted in vehicles, future mobility vehicles, or the like.

Hereinafter, a method of collecting odor data according to embodiments of the present invention using the above-described configuration will be described with reference to FIG. 5.

First, various kinds of standard gases, odors of which are to be measured, are manufactured (S101).

That is, various kinds of primary standard gases, the odors of which are to be measured, are manufactured, and manufacturing examples of the primary standard gases are shown in Table 1 below.

TABLE 1

| Component | Molecular Weight | Density | Reagent Purity [%] | Primary Standard Gas Manufacturing Concentration | | |
|---|---|---|---|---|---|---|
| | | | | Injection Amount [μl] | Bag Capacity [l] | Concentration [ppm] |
| Formaldehyde | 30.03 | 0.82 | 35.0 | 1,000.0 | 3.0 | 77,454.3 |
| Acetaldehyde | 44.05 | 0.78 | 85.0 | 20.0 | 3.0 | 2,465.7 |
| Acrolein | 56.07 | 0.84 | 90.0 | 50.0 | 3.0 | 5,487.8 |
| Propionaldehyde | 58.00 | 0.81 | 98.0 | 20.0 | 3.0 | 2,217.1 |
| Acetone | 58.08 | 0.78 | 99.5 | 10,000.0 | 3.0 | 1,095,335.2 |
| n-Butyl Acetate | 116.16 | 0.88 | 95.0 | 500.0 | 3.0 | 29,394.3 |
| Propionic Acid | 74.10 | 0.99 | 99.0 | 3.0 | 3.0 | 323.4 |
| n-Butyric Acid | 88.11 | 0.95 | 99.0 | 1.0 | 3.0 | 87.3 |
| Methanol | 21.04 | 0.79 | 99.9 | 5,000.0 | 10.0 | 459,720.4 |

The concentration (primary concentration) of each of various kinds of standard gases may be determined using Equation 1 below.

Equation 1:

$$\text{Primary Concentration} = \frac{(\text{Injection Amount}) \times (\text{Density}) \times 24.44 \times 1000}{(\text{Molecular Weight}) \times (\text{Bag Capacity}) \times (\text{Reagent Purity})}$$

In Table 1 and Equation 1 above, "bag capacity (l)" represents the capacity of a storage bag configured to store a primary standard gas, and "injection amount (μl)" represents an amount of gas injected into the storage bag at each injection time.

Subsequently, target concentrations for odor intensities of the standard gases are set in advance (S102).

The target concentrations for odor intensities may be set in advance as reference data by skilled odor panelists individually evaluating the odor intensities and concentrations of the standard gases. Examples of setting target concentrations for odor intensities of various kinds of standard gases are shown in Table 2 below.

TABLE 2

| Kind of Standard Gas | Odor Intensity (Bad Smell Intensity) | | | | | | |
|---|---|---|---|---|---|---|---|
| | 1 Target Concentration (ppm) | 2 Target Concentration (ppm) | 2.5 Target Concentration (ppm) | 3 Target Concentration (ppm) | 3.5 Target Concentration (ppm) | 4 Target Concentration (ppm) | 5 Target Concentration (ppm) |
| Formaldehyde | $4.1 \times 10^{-1}$ | 1.9 | 3.9 | 8.4 | 18 | 38 | 170 |
| Acetaldehyde | $1.5 \times 10^{-3}$ | $1.5 \times 10^{-2}$ | $4.7 \times 10^{-2}$ | $1.5 \times 10^{-1}$ | $4.6 \times 10^{-1}$ | 1.4 | 14 |
| Acrolein | $3.0 \times 10^{-2}$ | $1.4 \times 10^{-1}$ | $2.9 \times 10^{-1}$ | $6.3 \times 10^{-1}$ | 1.4 | 2.9 | 13 |
| Propionaldehyde | $1.5 \times 10^{-3}$ | $1.5 \times 10^{-2}$ | $4.6 \times 10^{-2}$ | $1.4 \times 10^{-1}$ | $4.5 \times 10^{-1}$ | 1.4 | 13 |
| Acetone | 30 | 110 | 210 | 400 | 760 | 1400 | 5200 |
| n-Butyl Acetate | $6.6 \times 10^{-2}$ | $5.0 \times 10^{-1}$ | 1.4 | 3.8 | 10 | 29 | 220 |
| Propionic Acid (Once) | $1.7 \times 10^{-3}$ | $8.4 \times 10^{-3}$ | $1.9 \times 10^{-2}$ | $4.1 \times 10^{-2}$ | $9.0 \times 10^{-2}$ | $2.0 \times 10^{-1}$ | $9.7 \times 10^{-1}$ |
| n-Butyric Acid (Once) | $9.6 \times 10^{-5}$ | $7.0 \times 10^{-4}$ | $1.9 \times 10^{-3}$ | $5.1 \times 10^{-3}$ | $1.4 \times 10^{-2}$ | $3.7 \times 10^{-2}$ | $2.7 \times 10^{-1}$ |
| Methanol | 57 | 200 | 374 | 700 | 1300 | 2500 | 8600 |

As shown in Table 2 above, odor intensity (bad smell intensity) may be classified into 1, 2, 2.5, 3, 3-5, 4, and 5, and the target concentration for odor intensity may increase from odor intensity 1 to odor intensity 5.

In detail, since the target concentration for odor intensity is set to increase from odor intensity 1 to odor intensity 5, odor intensity 1 corresponds to an odor that a person may barely feel, odor intensity 3 corresponds to an odor that a person may easily feel, and odor intensity 5 corresponds to an odor that a person may strongly feel.

For example, as shown in Table 2 above, when the standard gas is formaldehyde, the target concentration for odor intensity 1 may be set to $4.1 \times 10^{-1}$ ppm, the target concentration for odor intensity 3 may be set to 8.4 ppm, and the target concentration for odor intensity 5 may be set to 170 ppm.

Subsequently, the standard gases are metered in an amount corresponding to target concentrations for preset odor intensities (S103).

Examples of metering the standard gases in an amount corresponding to target concentrations (secondary concentrations) for preset odor intensities are shown in Tables 3A and 3B below.

TABLE 3A

| Component | Odor Intensity 2 | | | Odor Intensity 2.5 | | | Odor Intensity 3 | | |
|---|---|---|---|---|---|---|---|---|---|
| | Target Concentration [ppb] | Substantial Volume of Chamber [l] | Injection Amount [ml] | Target Concentration [ppb] | Substantial Volume of Chamber [l] | Injection Amount [ml] | Target Concentration [ppb] | Substantial Volume of Chamber [l] | Injection Amount [ml] |
| Formaldehyde | 1900.0 | 46.0 | 1.13 | 3900.0 | 46.0 | 2.316 | 8400 | 46.0 | 4.99 |
| Acetaldehyde | 15.0 | 46.0 | 0.28 | 47.0 | 46.0 | 0.88 | 150 | 46.0 | 2.80 |
| Acrolein | 140.0 | 46.0 | 1.17 | 290.0 | 46.0 | 2.43 | 630 | 46.0 | 5.28 |
| Propionaldehyde | 15 | 46.0 | 0.31 | 46 | 46.0 | 0.95 | 140 | 46.0 | 2.90 |
| Acetone | 110000 | 46.0 | 4.62 | 210000 | 46.0 | 8.82 | 400000 | 46.0 | 16.80 |
| n-Butyl Acetate | 500 | 46.0 | 0.78 | 1400 | 46.0 | 2.19 | 3800 | 46.0 | 5.95 |
| Propionic Acid | 8.4 | 46.0 | 1.19 | 19.0 | 46.0 | 2.70 | 41 | 46.0 | 5.83 |
| n-Butyric Acid | 0.7 | 46.0 | 0.37 | 1.9 | 46.0 | 1.00 | 5.1 | 46.0 | 2.69 |
| Methanol | 200000 | 46.0 | 20.0122 | 374000 | 46.0 | 37.4227 | 700000 | 46.0 | 70.0426 |

TABLE 3B

| Component | Odor Intensity 3.5 | | | Odor Intensity 4 | | |
|---|---|---|---|---|---|---|
| | Target Concentration [ppb] | Substantial Volume of Chamber [l] | Injection Amount [ml] | Target Concentration [ppb] | Substantial Volume of Chamber [l] | Injection Amount [ml] |
| Formaldehyde | 18000 | 46.0 | 10.690 | 38000 | 46.0 | 22.57 |
| Acetaldehyde | 460 | 46.0 | 8.58 | 1400 | 46.0 | 26.12 |
| Acrolein | 1400 | 46.0 | 11.74 | 2900 | 46.0 | 24.31 |
| Propionaldehyde | 450 | 46.0 | 9.34 | 1400 | 46.0 | 29.05 |
| Acetone | 760000 | 46.0 | 31.92 | 1400000 | 46.0 | 58.79 |
| n-Butyl Acetate | 10000 | 46.0 | 15.65 | 29000 | 46.0 | 45.38 |
| Propionic Acid | 90 | 46.0 | 12.80 | 200 | 46.0 | 28.45 |
| n-Butyric Acid | 14 | 46.0 | 7.38 | 37 | 46.0 | 19.51 |
| Methanol | 1300000 | 46.0 | 130.0791 | 2500000 | 46.0 | 250.1520 |

The target concentration (secondary concentration) for odor intensity may be determined using Equation 2 below.

$$\text{Intensity} = \frac{\substack{\text{(Injection Amount)} \times \\ \text{(Substantial Volume of Chamber =} \\ \text{Total Volume of Chamber} - \text{Volume of Sensor)}}}{\substack{\text{Concentration of Standard} \\ \text{Gas (Primary Concentration)}}}$$

$\qquad\qquad$ Target Concentration (Secondary Concentration) for Odor $\quad$ Equation 2

In Tables 3A and 3B and Equation 2 above, "injection amount (ml)" represents an amount of gas metered so as to correspond to a target concentration for specific odor intensity so as to be injected into the odor measurement chamber, and "substantial volume of chamber" represents a volume obtained by subtracting the volume of an internal odor sensor disposed in the odor measurement chamber from the total volume of the odor measurement chamber.

The injection amount (ml) of the gas injected into the odor measurement chamber, i.e., the amount of gas metered so as to correspond to a target concentration for specific odor intensity, needs to be determined based on the substantial volume of the odor measurement chamber.

Subsequently, a gas metered in an amount corresponding to a target concentration for specific odor intensity is injected into the odor measurement chamber (S104).

For example, the injector 140, which is a device such as a syringe, is inserted into the storage bag storing a primary standard gas to suction the standard gas in the storage bag. In this case, the injector 140 suctions the gas metered in an amount corresponding to a target concentration for preset odor intensity. Accordingly, the gas metered in an amount corresponding to a target concentration for preset odor intensity may be filled in the injector 140. Subsequently, the injection needle of the injector 140 may be inserted through the packing member in the gas injection hole 102 to inject the gas, the odor of which is to be measured, i.e., the gas metered in an amount corresponding to a target concentration for preset odor intensity, which is charged in the injector 140, into the odor measurement chamber 100.

Subsequently, two or more different types of internal odor sensors 200 disposed in the odor measurement chamber 100 may sense an odor of the gas (S105).

In detail, when the gas flow induction fan 230 of each of the internal odor sensors 200 is driven in response to a control signal of the controller, the gas, the odor of which is to be measured, i.e., the gas metered in an amount corresponding to a target concentration for specific odor intensity, which is injected into the odor measurement chamber 100 through the gas injection hole 102, may enter the gas inlet 212 of the first case 210 and then may flow to the gas outlet 214 via the first odor sensing portion 220. At this time, the first odor sensing portion 220 may sense an odor of the gas.

Further, the gas injected into the odor measurement chamber 100 may sequentially flow through the first gas circulation line 110 connected to the outside of the odor measurement chamber 100, the external odor sensor 300, and the second gas circulation line 120 and then may return back to the odor measurement chamber 100. At this time, the external odor sensor 300 may sense an odor of the gas (S106).

In detail, when the pump 330 of the external odor sensor 300 is driven in response to a control signal of the controller, the gas, the odor of which is to be measured, i.e., the gas metered in an amount corresponding to a target concentration for specific odor intensity, which is injected into the odor measurement chamber 100, may sequentially flow through the first gas circulation line 110 and the gas inlet 312 of the second case 310 and then may reach the second odor sensing portion 320. At this time, the second odor sensing portion 320 may sense an odor of the gas. Subsequently, the gas that has passed through the second odor sensing portion 320 may sequentially flow through the gas outlet 314, the second gas circulation line 120, and the return hole 106 and then may return back to the odor measurement chamber 100.

At this time, odor data of the gas sensed by the internal odor sensors 200 and odor data of the gas sensed by the external odor sensor 300 may be transmitted to and collected in the controller 400 (S107).

That is, odor data of the gas sensed by the internal odor sensors 200 and odor data of the gas sensed by the external odor sensor 300 may be transmitted to the controller 400 and may be stored in a memory of the controller.

In this way, the internal odor sensors 200 and the external odor sensor 300, which are of different types, may sense an odor of the gas having the same target concentration at the same time, whereby the sensing performance of the different types of odor sensors may be evaluated at once, and pieces of data on the odor sensed by the respective odor sensors may be collected at once. The collected odor data may be used as odor data for training artificial intelligence robots or the like or may be used as standard data for determination of the intensity and kind of odor measured by odor measurement devices mounted in vehicles, future mobility vehicles, or the like.

Meanwhile, the internal odor sensors 200 and the external odor sensor 300, which are disposed inside and outside the odor measurement chamber 100, may repeatedly sense an odor of a specific standard gas according to target concentrations for various odor intensities.

To this end, when the internal odor sensors 200 and the external odor sensor 300 sense an odor of a gas previously injected into the odor measurement chamber 100 (a gas metered in an amount corresponding to a target concentration for odor intensity lower by one level than that of a gas to be injected subsequently thereto, e.g., a gas having a target concentration corresponding to odor intensity 2) and data on the sensed odor is completely collected in the controller, a new gas (a gas metered in an amount corresponding to a target concentration for odor intensity higher by one level than that of the gas injected prior thereto, e.g., a gas having a target concentration corresponding to odor intensity 2.5) needs to be injected into the odor measurement chamber 100 so that the odor thereof is sensed.

For example, as shown in Tables 3A and 3B above, in the case of formaldehyde among various kinds of standard gases, the target concentration for odor intensity 2 is 1900.0 ppb, and the injection amount of the gas injected into the odor measurement chamber (the amount of gas metered so as to correspond to a target concentration for the corresponding odor intensity) is 1.13 ml. However, because the target concentration for odor intensity 2.5 is 3900.0 ppb, the injection amount of a gas that is to be newly injected into the odor measurement chamber (the amount of gas metered so as to correspond to a target concentration for the corresponding odor intensity) needs to be increased to 2.316 ml.

In this case, when a gas metered in an amount corresponding to a target concentration for odor intensity higher by one level is newly injected into the odor measurement chamber 100, the amount of gas to be newly injected into the odor measurement chamber 100 may be equivalent to an amount obtained by subtracting the amount of gas metered so as to correspond to a target concentration for odor intensity lower by one level, i.e., the amount of gas previously injected into the odor measurement chamber 100, from the amount of gas metered so as to correspond to a target concentration for odor intensity higher by one level.

For example, in the case of formaldehyde among various kinds of standard gases, the amount of gas having a target concentration (1900.0 ppb) for odor intensity 2, i.e., the amount of gas previously injected into the odor measurement chamber 100, is 1.13 ml, and the amount of gas having a target concentration (3900.0 ppb) for odor intensity 2.5, i.e., the amount of gas to be newly injected into the odor measurement chamber 100, is 2.316 ml. In this case, since 1.13 ml of formaldehyde gas is already present in the odor measurement chamber 100, 1.186 ml of formaldehyde gas, which is obtained by subtracting 1.13 ml from 2.316 ml, may be additionally injected into the odor measurement chamber 100.

In this way, when a gas metered in an amount corresponding to a target concentration for odor intensity higher by one level is newly injected into the odor measurement chamber 100 in order to repeatedly measure an odor of the corresponding standard gas according to target concentrations for various odor intensities, the gas is additionally injected into the odor measurement chamber 100 by an amount that is obtained by subtracting the amount of gas metered so as to correspond to a target concentration for odor intensity lower by one level, i.e., the amount of gas previously injected into the odor measurement chamber 100, from the amount of gas metered so as to correspond to a target concentration for odor intensity higher by one level. Accordingly, a standard gas reagent may be saved, and odor measurement tests may be continuously carried out without unnecessary waste of the standard gas reagent.

As is apparent from the above description, embodiments of the present invention have the following effects.

First, after target concentrations for odor intensities of various kinds of gases, the odors of which are to be measured, are set in advance, a specific gas is metered in an amount corresponding to a target concentration for preset odor intensity, and the odor of the gas is sensed by different types of odor sensors, whereby data on the odor sensed by the odor sensors may be collected regardless of the type or kind of odor sensor, and the collected odor data may be used as standard data for determination of the intensity and kind of odor.

Second, since different types of odor sensors sense an odor of the same gas at the same time, the sensing performance of the different types of odor sensors may be evaluated at once and pieces of data on the odor sensed by the respective odor sensors may be collected at once.

Third, the collected data on the odor sensed by the different types of odor sensors may be used as odor data for training artificial intelligence robots or the like or may be used as standard data for determination of the intensity and kind of odor measured by odor measurement devices mounted in vehicles, future mobility vehicles, or the like.

Embodiments of the present invention have been described above with reference to exemplary embodiments. The embodiments described in the specification and shown in the accompanying drawings are illustrative only and are not intended to represent all aspects of all embodiments of the invention. Therefore, the embodiments of the present invention are not limited to the embodiments presented herein, and it is to be understood by those skilled in the art that various modifications or changes can be made without departing from the technical spirit or scope of the invention as disclosed in the appended claims.

What is claimed is:

1. A device for collecting odor data, the device comprising:
   an odor measurement chamber comprising a gas injection hole;
   a first gas circulation line and a second gas circulation line selectively connected to the odor measurement chamber;
   internal odor sensors disposed in the odor measurement chamber, wherein the internal odor sensors are of different types from each other; and
   an external odor sensor disposed outside the odor measurement chamber and connected to the first gas circulation line and the second gas circulation line.

2. The device of claim 1, further comprising an injector connected to the gas injection hole, the injector being configured to inject a gas into the odor measurement chamber.

3. The device of claim 2, wherein the injector is filled with the gas metered in an amount corresponding to a target concentration for a preset odor intensity.

4. The device of claim 1, wherein each of the internal odor sensors comprises:
   a first case comprising a gas inlet and a gas outlet provided in respective ends thereof;
   a first odor sensing portion disposed in the first case between the gas inlet and the gas outlet, the first odor sensing portion being configured to sense an odor of a gas; and
   a gas flow induction fan mounted in the gas inlet or the gas outlet.

5. The device of claim 1, wherein the external odor sensor comprises:
   a second case comprising a gas inlet and a gas outlet provided in respective ends thereof;
   first connectors mounted to the gas inlet and the gas outlet, the first connectors being configured to be coupled to second connectors mounted to the first gas circulation line and the second gas circulation line, respectively;
   a second odor sensing portion disposed in the second case so as to be located between the gas inlet and the gas outlet, the second odor sensing portion being configured to sense an odor of a gas; and
   a pump mounted in the gas inlet or the gas outlet, the pump being configured to circulate the gas in the odor measurement chamber so that the gas sequentially flows through the first gas circulation line, the second odor sensing portion, and the second gas circulation line and returns back to the odor measurement chamber.

6. The device of claim 1, further comprising a controller configured to collect data on an odor sensed by the internal odor sensors and the external odor sensor.

7. The device of claim 1, further comprising a door mounted on one side portion of the odor measurement chamber, wherein the door is configured to provide a passage for replacement of the internal odor sensors.

8. A method of collecting odor data, the method comprising:
   injecting a gas metered in an amount corresponding to a target concentration for a preset odor intensity into an odor measurement chamber;

sensing, by internal odor sensors disposed in the odor measurement chamber, an odor of the gas, wherein the internal odor sensors are of different types from each other;

sensing, by an external odor sensor, the odor of the gas during a process in which the gas injected into the odor measurement chamber sequentially flows through a first gas circulation line connected to an outside of the odor measurement chamber, the external odor sensor, and a second gas circulation line and returns back to the odor measurement chamber; and collecting, by a controller, data on the odor sensed by the internal odor sensors and the external odor sensor.

9. The method of claim 8, further comprising obtaining the gas metered in the amount corresponding to the target concentration for the preset odor intensity, wherein obtaining the gas comprises:

manufacturing various kinds of standard gases;

setting target concentrations for odor intensities of the standard gases in advance; and metering the standard gases in an amount corresponding to the set target concentrations for odor intensities.

10. The method of claim 8, further comprising:

determining an amount of the gas to be metered that corresponds to the target concentration for the preset odor intensity plus an additional amount;

subtracting the amount of the gas already injected into the odor measurement chamber from the amount of the gas to be metered that corresponds to the target concentration for the preset odor intensity plus the additional amount to obtain a subsequent amount of the gas to be injected; and injecting the subsequent amount of the gas into the odor measurement chamber.

11. The method of claim 8, wherein each of the internal odor sensors comprises:

a first case comprising a gas inlet and a gas outlet provided in respective ends thereof;

a first odor sensing portion disposed in the first case between the gas inlet and the gas outlet, wherein the first odor sensing portion senses the odor of the gas; and a gas flow induction fan mounted in the gas inlet or the gas outlet.

12. The method of claim 11, wherein the external odor sensor comprises:

a second case comprising a second gas inlet and a second gas outlet provided in respective ends thereof;

first connectors mounted to the second gas inlet and the second gas outlet, wherein the first connectors are coupled to second connectors mounted to the first gas circulation line and the second gas circulation line, respectively;

a second odor sensing portion disposed in the second case between the second gas inlet and the second gas outlet, wherein the second odor sensing portion senses the odor of the gas; and a pump mounted in the second gas inlet or the second gas outlet, wherein the pump circulates the gas in the odor measurement chamber so that the gas sequentially flows through the first gas circulation line, the second odor sensing portion, and the second gas circulation line and returns back to the odor measurement chamber.

13. The method of claim 8, wherein the external odor sensor comprises:

a case comprising a gas inlet and a gas outlet provided in respective ends thereof;

first connectors mounted to the gas inlet and the gas outlet, wherein the first connectors are coupled to second connectors mounted to the first gas circulation line and the second gas circulation line, respectively;

a second odor sensing portion disposed in the second case between the gas inlet and the gas outlet, wherein the second odor sensing portion senses the odor of the gas; and a pump mounted in the gas inlet or the gas outlet, wherein the pump circulates the gas in the odor measurement chamber so that the gas sequentially flows through the first gas circulation line, the second odor sensing portion, and the second gas circulation line and returns back to the odor measurement chamber.

14. A system for collecting odor data, the system comprising:

an odor measurement chamber comprising a gas injection hole, a discharge hole, and a return hole;

internal odor sensors disposed in the odor measurement chamber, wherein the internal odor sensors are of different types from each other, and wherein the internal odor sensors are configured to sense an odor of a gas injected into the odor measurement chamber;

an external odor sensor disposed outside the odor measurement chamber, wherein the external odor sensor is configured to sense the odor of the gas;

a first gas circulation line having a first end connected to the discharge hole and a second end connected to the external odor sensor;

a second gas circulation line having a first end connected to the return hole and a second end connected to the external odor sensor; and a controller configured to collect data on the odor sensed by the internal odor sensors and the external odor sensor.

15. The system of claim 14, further comprising an injector connectable to the gas injection hole, the injector being configured to inject the gas into the odor measurement chamber.

16. The system of claim 15, wherein the injector is filled with the gas metered in an amount corresponding to a target concentration for a preset odor intensity.

17. The system of claim 14, wherein each of the internal odor sensors comprises:

a first case comprising a gas inlet and a gas outlet provided in respective ends thereof;

a first odor sensing portion disposed in the first case between the gas inlet and the gas outlet, the first odor sensing portion being configured to sense the odor of the gas; and a gas flow induction fan mounted in the gas inlet or the gas outlet.

18. The system of claim 14, wherein the external odor sensor comprises:

a second case comprising a second gas inlet and a second gas outlet provided in respective ends thereof;

first connectors mounted to the second gas inlet and the second gas outlet, the first connectors being configured to be coupled to second connectors mounted to the first gas circulation line and the second gas circulation line, respectively;

a second odor sensing portion disposed in the second case between the second gas inlet and the second gas outlet, the second odor sensing portion being configured to sense the odor of the gas; and a pump mounted in the second gas inlet or the second gas outlet, the pump being configured to circulate the gas in the odor measurement chamber so that the gas sequentially flows through the first gas circulation line, the second odor sensing portion, and the second gas circulation line and returns back to the odor measurement chamber.

19. The system of claim 14, further comprising a door mounted on one side portion of the odor measurement chamber, wherein the door is configured to provide a passage for replacement of the internal odor sensors.

\*    \*    \*    \*    \*